United States Patent [19]

Asano et al.

[11] 4,345,101
[45] Aug. 17, 1982

[54] PROCESS FOR PURIFYING AN AQUEOUS SOLUTION OF ACRYLAMIDE

[75] Inventors: Shiro Asano, Takaishi; Kohei Shizuka; Yoshihiko Kambara, both of Chiba; Junji Mikami; Hiroshi Kato, both of Takaishi; Tadatoshi Honda, Kanagawa, all of Japan

[73] Assignee: Mitsui Toatsu Chemicals, Inc., Tokyo, Japan

[21] Appl. No.: 269,602

[22] Filed: Jun. 2, 1981

[30] Foreign Application Priority Data

Jun. 18, 1980 [JP] Japan ................................ 55-81384

[51] Int. Cl.³ ........................................ C07C 103/133
[52] U.S. Cl. ................................................. 564/206
[58] Field of Search ......................................... 564/206

[56] References Cited

U.S. PATENT DOCUMENTS

| 2,865,960 | 12/1958 | Shearer et al. | 564/206 |
| 3,941,837 | 2/1976 | Asano et al. | 564/206 |
| 4,032,572 | 6/1977 | Asano et al. | 564/206 |
| 4,108,893 | 8/1978 | Asano et al. | 564/206 |
| 4,302,600 | 11/1981 | Saitoh et al. | 564/206 |

Primary Examiner—Arthur P. Demers
Attorney, Agent, or Firm—Fisher, Christen & Sabol

[57] ABSTRACT

An aqueous solution of acrylamide obtained by catalytic hydration of acrylonitrile in the presence of a copper-based catalyst is purified by the steps, in sequence, of (a) removal of the unreacted acrylonitrile, (b) removal of copper, (c) treatment under basic conditions, (d) cation exchanging treatment and (e) weakly basic anion exchanging treatment. The acrylamide obtained by this process has good storage stability. An acrylamide polymer produced from this monomer is useful as a flocculant having a reduced content of the unreacted monomer, a high molecular weight and excellent solubility in water.

9 Claims, No Drawings

PROCESS FOR PURIFYING AN AQUEOUS SOLUTION OF ACRYLAMIDE

BACKGROUND OF THE INVENTION

1. Field of the Invention

This invention relates to a process for purifying an aqueous solution of acrylamide obtained by the catalytic hydration of acrylonitrile with water in the presence of a copper-based catalyst.

2. Description of the Prior Art

Acrylamide has been used as acrylamide polymers which are useful as papermaking chemicals, flocculants, oil recovery additives, soil hardeners, etc., and has also found wide applications as a comonomer for other polymers. Early production of acrylamide was by the so-called sulfuric acid process. Recently, a process involving catalytic hydration of acrylonitrile in the presence of a copper-based catalyst was developed, and has now superseded the sulfuric acid process in industrial production.

Flocculants, as one use of acrylamide mentioned above, have recently found wider applications in waste water treatment, etc., and considerable efforts have been directed to improvement of their quality and performance. In particular, the molecular weight of acrylamide polymers used as flocculants, which is said to contribute directly to the performance of flocculants, has tended to become higher, and high molecular weights of more than 10 million, particularly about 14 million, are currently sought. This is very unique in view of the fact that molecular weights required of acrylamide polymers for other uses or of other polymers are usually less than one million. In addition, since as flocculants, acrylamide polymers are normally used in the form of an aqueous solution, they are required to dissolve rapidly in water without leaving any insoluble portion. Moreover, because of the toxicity of the acrylamide monomer, the content of the unreacted monomer remaining in the polymer is required to be very low, for example, not more than 0.2%. Usually, however, these requirements are difficult to fulfill together with the requirement for increasing the molecular weight, and a great deal of effort has been made to achieve these improvements simultaneously.

The "molecular weights", as used in this application, refer to those determined by the test method shown in Example 1 given hereinbelow. The "water solubility of an acrylamide polymer", as used in this application, refers mainly to that of a dry powder having a water content of not more than 20% by weight, especially about 10% by weight, obtained by drying a polymer prepared usually in an aqueous medium.

Many suggestions have been made about the production of high-molecular-weight acrylamide polymers having good water solubility. They include, for example, the addition of urea-type compounds, various amines, nitrilotriscarboxylic acids, etc., as an insolubilization inhibitor before, during or after the polymerization reaction of acrylamide; the use of a specified polymerization initiator system such as a combination of a cerium salt and acetylacetone or a combination of an oil-soluble azo compound and an amine; and a method in which drying of a hydrogel obtained by the polymerization reaction is effected by jointly using extractive dehydration with a solvent, or the drying is effected in two stages under different conditions.

It is recognized that the solution to the aforesaid problem depends not only upon the method of production of acrylamide polymers, but also greatly upon the quality of acrylamide. For example, Japanese Laid-Open Patent Publication No. 68118/1977 states that the acrolein content of the starting acrylonitrile should be not more than 1.5 ppm, and Japanese Laid-Open Patent Publication No. 138585/1977 states that the 3,3',3"-nitrilotrispropionic acid content in acrylamide should be adjusted to 0.1 ppm or below. Thus, even about 1 ppm of an organic impurity in acrylamide or in the starting acrylonitrile is regarded as being toxic, and a very high degree of purification would be necessary. As is well known, acrylamide is a very reactive compound which undergoes vinyl-type polymerization reaction, carbamoyethylation, a reaction involving transfer of hydrogen of the amide group, etc. Hence, it is likely to induce such reactions during purification to generate new impurities.

From this standpoint, the crystallization method heretofor practiced for purification of acrylamide is an accurate and superior method, but adds greatly to the cost of production. This is because by the catalytic hydration process, acrylamide is inevitably formed in aqueous solution and is marketed as such, while on the other hand, acrylamide polymers are most generally produced by aqueous solution polymerization or oil-in-water emulsion polymerization using acrylamide in the form of an aqueous solution. In view of this, the inclusion of a crystallization step in the process of producing acrylamide monomer is very uneconomical.

Many methods have been proposed for purifying acrylamide obtained by the catalytic hydration process while it is in the form of an aqueous solution. They include, for example, a method which comprises distilling off the unreacted acrylonitrile together with a part of water under weakly basic conditions (Japanese Laid-Open Patent Publication No. 56914/1974), a method which comprises eliminating copper using a specified cation exchange resin (Japanese Laid-Open Patent Publication No. 62929/1975), a method which comprises maintaining the acrylamide solution under basic conditions while blowing an inert gas thereinto (Japanese Laid-Open Patent Publication No. 133318/1974), a method which comprises treating the acrylamide solution with a strongly basic anion exchange resin (Japanese Laid-Open Patent Publication No. 82011/1975), and a method which comprises subjecting the acrylamide solution to air treatment and treatment with a strongly acidic cation exchange resin, followed by treatment with a weakly basic anion exchange resin (Japanese Laid-Open Patent Publication No. 100418/1977).

The present inventors investigated these methods and their combinations in detail, but failed to find a method for purifying acrylamide which is suitable for production of the aforesaid high-molecular-weight acrylamide polymer. When a dry powdery product of a high-molecular-weight acrylamide polymer is produced by using the acrylamide purified by the above methods, its quality, especially its water solubility, is frequently unsatisfactory. Furthermore, when the above acrylamide is stored for a long period of time as an aqueous solution, it is degraded during storage, and polymers produced from the stored acrylamide have reduced solubility in water.

SUMMARY OF THE INVENTION

This invention contemplates the provision of an improved process for purifying an aqueous solution of acrylamide obtained by the catalytic hydration of acrylonitrile with water in the presence of a copper-based catalyst.

It is a first objective of this invention to provide acrylamide suitable for the production of high-molecular-weight acrylamide polymers which have a molecular weight of at least 10 million, especially about 14 million, are easily soluble in water, and have an unreacted monomer content of, for example, as low as not more than 0.2% by weight.

A second objective of the invention is to provide a process for purifying an aqueous solution of acrylamide to give a purified product which does not undergo degradation in quality when stored for a long period of time in the form of an aqueous solution prior to being used for the production of acrylamide polymers.

The above objectives of the invention are achieved by subjecting an aqueous solution of crude acrylamide obtained by the catalytic hydration of acrylonitrile with water in the presence of a copper-based catalyst, in sequence, to (a) a step of distilling off substantially all of the unreacted acrylonitrile, (b) a step of removing substantially all of the copper, (c) a step of allowing the aqueous solution of acrylamide to stand under basic conditions, (d) a step of cation exchanging treatment and (e) a step of weakly basic anion exchanging treatment.

DETAILED DESCRIPTION OF THE INVENTION

Acrylonitrile synthesized by so-called ammoxidation of propylene is usually employed as the starting acrylonitrile in the process of this invention. In order, however, to use it in synthesizing acrylamide suitable for production of high-molecular-weight acrylamide polymers, there are some restrictions on its impurities, as is already known. Specifically, acrylonitrile used in the process of the invention preferably has an acrolein content of not more than 1.5 ppm, a hydroquinone content of not more than 0.2 ppm and an oxazole content of not more than 25 ppm. Acrylonitrile marketed for industrial use usually contains about 40 ppm of p-methoxyphenol as a stabilizer. It may be used as such or after its p-methoxyphenol content is reduced to below this level.

Examples of the copper-based catalyst used in the process of the invention are (A) a combination of copper in the form of a copper wire, a copper powder, etc., with a copper ion, (B) reduced copper obtained by reducing a copper compound with a reducing agent, (C) decomposed copper obtained by decomposing a copper compound with heat, etc., and (D) Raney copper obtained by leaching a Raney alloy of copper with an alkali, etc. The reduced copper is produced, for example, by (1) a method which comprises reducing copper oxide in the gaseous phase with hydrogen, carbon monoxide or ammonia, (2) a method which comprises reducing a salt or hydroxide of copper in aqueous solution with formaldehyde, hydrazine or sodium borohydride, and (3) a method which comprises reducing a salt or hydroxide of copper in aqueous solution with elemental aluminum, zinc or iron. The main catalytic ingredient of the products is considered to be elemental copper. The decomposed copper is produced, for example, by (1) a method which comprises thermally decomposing, in aqueous alkali, copper hydroxide obtained by treating a copper compound with sodium hypophosphite, etc., (2) a method which comprises thermally decomposing copper formate or copper oxalate, (3) a method which comprises thermally decomposing the so-called cluster copper shown in Japanese Laid-Open Patent Publication No. 108015/1974, and (4) a method which comprises adding copper acetylide or copper nitride directly to the hydration reaction system of acrylonitrile. The main catalytic ingredient of the products including that in method (4) is considered to be elemental copper. Production of the Raney copper is, for example, by (1) a method which comprises nearly completely leaching a copper-aluminum alloy with sodium hydroxide, sulfuric acid, water, an organic amine, etc., and (2) a method which comprises partially leaching a copper-aluminum alloy with sodium hydroxide, sulfuric acid, water, an organic amine, etc., leaving a part of the aluminum together with copper. The main catalytic ingredient of the products is considered to be elemental copper. These copper-based catalysts may be supported on ordinary carriers, and may contain metals other than copper, such as chromium or molybdenum. Desirably, the catalyst should be kept from contact with oxygen and oxygen-containing gases before and during use, because oxygen impairs the catalytic activity of these catalysts and increases the amounts of by-products such as ethylene cyanohydrin.

The hydration of acrylonitrile in this invention is carried out in the following manner in the presence of the aforesaid copper-based catalyst. The reaction is performed in the liquid phase in a suspended or fixed catalyst bed by a flowing or batchwise method. The weight ratio between acrylonitrile and water used in the hydration reaction is substantially optional. Preferably, the weight ratio of acrylonitrile to water is from 60:40 to 5:95, more preferably from 50:50 to 10:90. The reaction temperature in the hydration reaction is preferably 50° to 200° C., more preferably 70° to 150° C. The conversion of acrylonitrile is preferably 10 to 98%, more preferably 30 to 95%.

At the aforesaid acrylonitrile-to-water weight ratio, reaction temperature and acrylonitrile conversion, the unreacted acrylonitrile, the unreacted water and the resulting acrylamide sometimes do not form a homogeneous solution. To avoid this, acrylamide or another cosolvent may be added. The inside of the reactor is maintained at a pressure which is the vapor pressure at the aforesaid temperature and reactant ratio with or without the pressure of an inert gas such as nitrogen added thereto. This pressure is usually from atmospheric pressure to 10 atmospheres. Dissolved oxygen contained in the catalyst, acrylonitrile, water, the solvent, etc., to be fed into the reactor should desirably be removed fully before these materials are fed into the reactor, because it increases the amounts of by-products such as ethylene cyanohydrin. For the same reason, the inside of the reactor is maintained in an oxygen-free atmosphere. The reaction solution withdrawn from the reactor after the hydration reaction consists mainly of the unreacted acrylonitrile, the unreacted water, acrylamide and the cosolvent (if used) other than acrylamide, and further contains minor amounts of by-products such as ethylene cyanohydrin, and copper.

The main purpose of utilizing acrylamide obtained by the process of this invention is to produce high-molecular-weight acrylamide polymers for use as flocculants, etc. A process for production of these polymers is briefly described below.

Acrylamide is used either singly or together with a vinyl polymerization-type comonomer. Examples of the comonomer are acrylic acid and methacrylic acid and the water-soluble salts thereof; alkylaminoalkyl esters of acrylic and methacrylic acids, or the quaternary ammonium derivatives thereof; N-(dimethylaminopropyl) methacrylamide or the quaternary ammonium derivatives thereof; vinyl acetate; and acrylonitrile. The proportion of the comonomer is usually not more than 100 moles, particularly not more than 50 moles, per 100 moles of acrylamide.

Polymerization of acrylamide and the comonomer is carried out by known methods such as aqueous solution polymerization and emulsion polymerization methods. A general procedure of the aqueous polymerization technique which is most widely used is described below. Usually, the total concentration of acrylamide and the comonomer in the solution is preferably in the range of 5 to 60% by weight. As a polymerization initiator, there are used, for example, peroxides such as potassium persulfate, ammonium persulfate, hydrogen peroxide and benzoyl peroxide; azo-type free radical initiators such as azobisisobutyronitrile, 2,2'-azobis(2-amidinopropane) dihydrochloride and 4,4'-azobis(sodium 4-cyanovalerate); and Redox systems composed of the aforesaid peroxides and reducing agents such as sodium bisulfite, triethanolamine and ferrous ammonium sulfate. When the total concentration of acrylamide and the comonomer is at least 15% by weight and the resulting polymer has a molecular weight of as high as at least 10 million, the polymerization temperature is difficult to control by cooling, etc. Accordingly, the polymerization is usually carried out in an adiabatic polymerization mode. In this case, the temperature of the polymerization system rises by the heat of polymerization as the polymerization proceeds. In many cases, the temperature at the initiation of the polymerization is selected from the range of $-5°$ to $40°$ C., and the temperature upon completion of the reaction reaches as high as $55°$ to $100°$ C., for example.

To increase the molecular weight to at least 10 million, particularly as high as about 14 million, ingenuity is exercised concerning the total concentration of acrylamide and the comonomer, the type and concentration of the polymerization initiator, the reaction temperature, etc. Similar ingenuity is exercised in order to adjust the content of the unreacted acrylamide in the polymer to a small value of, for example, not more than 0.2%, and particularly a method is employed in which two or more polymerization initiators are caused to act in different temperature regions.

The aforesaid polymerization gives a hydrogel which is a rubbery gel containing nearly all of the water used to form the aqueous solution of acrylamide and the comonomer. Usually, the hydrogel is dehydrated by water extraction or heat drying or the hydrogel or dry gel is crushed or pulverized, in order to obtain a dry powdery product. Sometimes, before or during these treatments, the acrylamide polymer may be chemically modified by, for example, kneading sodium hydroxide into the hydrogel and heating the mixture to change a part of the amide group to a carboxyl group.

As a result of increasing the molecular weight, decreasing the content of the unreacted monomers and drying and powderizing the polymer or at times chemically modifying the polymer by the methods described above, the acrylamide polymer frequently becomes difficult to dissolve in water and tends to lose its value as merchandise such as flocculants. To overcome this disadvantage, there are practiced, as described hereinabove, the method comprising adding an insolubilization inhibitor before, during or after the polymerization reaction, the method comprising using a specified polymerization initiator system, the method which comprises performing the drying of the hydrogel under specified conditions, etc.

Now, the purifying procedure which constitutes the characterizing part of the present invention is described more specifically below.

(a) Step of distilling off substantially all of the unreacted acrylonitrile

The aqueous solution of crude acrylamide obtained by the catalytic hydration of acrylonitrile consists mainly of the unreacted acrylonitrile, the unreacted water, acrylamide and cosolvent (if used) other than acrylamide. This aqueous solution is subjected to an evaporation or distillation operation by an ordinary method or a method specially designed for the purpose of inhibiting polymerization, etc., thereby recovering the unreacted acrylonitrile and a part of the water and obtaining a concentrated aqueous solution of acrylamide. Usually, the recovered acrylonitrile and water are again used as materials in the hydration reaction. Inclusion of a large amount of acrylonitrile in the resulting aqueous solution of acrylamide is very detrimental to the quality of the obtained acrylamide in regard to the additional steps of the present invention. Investigations of the present inventors have shown that substantially all of the unreacted acrylonitrile should be distilled off, and the allowable amount of remaining acrylonitrile should be not more than 1,000 ppm, preferably not more than 100 ppm, more preferably not more than 20 ppm, especially preferably not more than 10 ppm, based on the acrylamide.

The concentration of the aqueous solution of acrylamide obtained in this step is usually in the range of 10 to 50% by weight. If the concentration of the aqueous solution of acrylamide exceeds 60% by weight, difficulty arises in the process of polymerizing acrylamide. Concentrations below 10% by weight do not cause immediate disadvantages, but are not preferred because the aqueous solution must be concentrated in order to perform the subsequent steps or to produce acrylamide polymers economically.

(b) Step of removing substantially all of the copper (copper eliminating treatment)

The aqueous solution of acrylamide obtained by the removal of acrylonitrile in step (a) usually contains 10 to 1,000 ppm (based on pure acrylamide; the same basis applies hereinafter) of copper. The form of copper is not clear, but the copper is considered to comprise a nonionic copper such as colloidal particles of elemental copper as well as a copper ion or copper complex ion. Since the presence of such a large amount of copper hampers the normal functioning of the subsequent treatment steps and reduces the quality of the resulting aqueous solution of acrylamide, the content of copper should be decreased to preferably not more than 25 ppm, more preferably to not more than 10 ppm, especially preferably to not more than 1 ppm. A method involving using a cation exchange resin and a method involving using a chelate resin are widely known and are superior for removing copper from an aqueous solution of acrylamide. In the present invention, too, these two methods are employed. The nonionic copper as such cannot be removed, or is difficult to remove, by these copper eliminating treatments. But the nonionic copper can be easily removed if it is rendered ionic by contacting it with oxygen gas, for example.

Various known cation exchange resins and chelate resins are used. As the cation exchange resins, both strongly acidic cation exchange resins and weakly acidic action exchange resins can be used, but the former are easier to use. They may be gelled resin or porous resins. Specific examples include Amberlite IR 120B and IRC 50 (tradenames for products of Rohm & Haas Company), Diaion SKIB PK 208 and WK 10 (tradenames for products of Mitsubishi Chemical Industries, Ltd.), and Lewatit SP100, SP112 and CNP80 (tradenames for products of Bayer AG). These cation exchange resins may be in the form of a free acid or a salt such as a sodium salt, but free acid-type cation exchange resins are convenient to use.

Resins obtained by introducing various chelate-forming groups into a styrene-divinylbenzene polymer, and various other resins are known as the chelate resins. Preferred are those obtained by introducing chelate-forming groups into a styrene/divinylbenzene polymer. Specific examples are Diaion CR-10 (a tradename for a product of Mitsubishi Chemical Industries, Ltd.) and Lewatit TP-207 (a tradename for a product of Bayer AG). Usually, these chelate resins are used in the form of sodium salt.

In performing the copper eliminating treatment, the cation exchange resin or chelate resin is used in any of a fixed bed, moving bed and suspended bed, but the fixed bed is the best. The concentration of the aqueous acrylamide solution to be subjected to the copper eliminating treatment is preferably 10 to 60% by weight for the same reason as in the step (a). The temperature for the copper eliminating treatment is preferably not more than 40° C. in order to maintain the aqueous acrylamide solution stable. Furthermore, since an aqueous solution of acrylamide has its own acrylamide-precipitating temperature according to its concentration, the copper eliminating temperature should be higher than the acrylamide-precipitating temperature. The pH of the aqueous solution of acrylamide before treatment is preferably 2 to 10, more preferably 3 to 9, in order to maintain the aqueous solution of acrylamide stable, but is also restricted by the preferred pH range inherent to a particular type of the cation exchange resin or chelate resin used. The cation exchange resin or chelate resin which has lost its ability to eliminate copper with the lapse of time is regenerated with chemicals in a customary manner, and then re-used.

(c) Step of allowing the residue to stand under basic conditions (base treatment)

A basic compound is then added to the aqueous solution of acrylamide obtained by the copper eliminating treatment in (b) to render it basic, and then the solution is allowed to stand under a prescribed set of conditions.

Prior to the present invention, the present inventors noted and investigated the process disclosed in Japanese Patent Publication No. 41847/1977 which is a process for purifying acrylamide comprising adding 0.1 to 1.5% by weight, based on acrylamide, of an inorganic base excluding ammonia at a temperature of up to 60° C. to an aqueous solution of acrylamide having a concentration of 15 to 60% by weight, and blowing a gas inert to acrylamide into the mixture at a hydrogen ion concentration (pH) of 12 to 13.7. The investigations showed that although this process is effective to some extent, when the resulting acrylamide is used in the production of a high-molecular-weight acrylamide polymer intended by this invention, the resulting polymer does not have satisfactorily good water solubility. The present inventors also investigated the process of Japanese Patent Publication No. 28777/1977, similar to the above process, which is a process for producing a concentrated aqueous solution of acrylamide comprising removing water by evaporation from a dilute aqueous solution of acrylamide to which is added at least one compound selected from alkali metal hydroxides, carbonates and bicarbonates and alkaline earth metal hydroxides. They found, however, that this process can not give acrylamide suitable for production of high-molecular-weight acrylamide polymers.

Thus, the present inventors have discovered that the objects of this invention can be fully achieved only by performing a series of the treatment steps in accordance with this invention.

Examples of basic compounds used in this invention in step (c) are alkali metal hydroxides and carbonates, alkaline earth metal hydroxides, ammonia and organic amines. Sodium hydroxide, potassium hydroxide, calcium hydroxide, sodium carbonate and potassium carbonate are preferred.

The amount of the basic compound is selected such that the pH of the solution after its addition is 11.5 to 14.0, preferably 12.0 to 13.5. If the pH is below 11.5, no sufficient treating effect can be obtained. If, on the other hand, the pH is more than 14.0, acrylamide becomes unstable and induces undesirable side-reactions. In the process of this invention, the aqueous solution of acrylamide is usually allowed to stand while maintaining the pH of the solution within this range. An operation of blowing an inert gas such as nitrogen or air into the solution or an operation of evaporating off water from the solution by heating is unnecessary except where an oxygen-containing gas is blown into the solution to inhibit polymerization of acrylamide. Rather, such an operation may result in a decrease in pH, and it then becomes necessary to feed in an additional supply of the basic compound. This undesirably reduces the effects of both the subsequent cation exchanging treatment and the weakly basic anion exchanging treatment.

In other words, in the process of this invention a small amount of an oxygen-containing gas, which can inhibit polymerization of the aqueous acrylamide solution, for example which can maintain the concentration of dissolved oxygen in the solution substantially saturated, may be blown as required into the aqueous acrylamide solution. However, it is not necessary to perform the base treatment while blowing a large amount of an inert gas such as air, thereby removing the ammonia generated.

The concentration of the aqueous acrylamide solution used in the base treatment is preferably in the range of 10 to 60% by weight for the same reason as in step (a). The temperature of the base treatment is 70° C. to 0° C., preferably 50° C. to 5° C., more preferably 40° C. to 10° C., in order to maintain the aqueous solution of acrylamide stable. Since the aqueous solution of acrylamide has its own acrylamide-precipitating temperature according to its concentration, the temperature of the base treatment should be higher than the acrylamide-precipitating temperature.

The base treatment can be carried out by a flowing or batchwise method. An ordinary agitating vessel can be used as an apparatus for the flowing method. Furthermore, an apparatus generally designed to inhibit backmixing, such as at least two series-connected agitating vessels, tubes, packed towers, plate towers, etc. can also be used and this method is preferred.

The treating time by the flowing method varies depending upon the pH, the temperature and the type of apparatus. Generally, the suitable treating time is 0.5 to 24 hours, preferably 0.5 to 10 hours. Suitable conditions may be selected by performing the treatment for a shorter period of time at a higher pH and a higher temperature, or for a longer period of time at a lower pH and a lower temperature. Of course, periods of time outside this range may be used. But if the time is too short, the effect of the treatment is insufficient. Too long a period of time, on the other hand, cannot bring about the expected treating effect, and may induce unwanted side-reactions.

An ordinary vessel can be used as an apparatus for the batchwise method. As in the flowing method, the treating time is preferably in the range of 0.5 to 10 hours.

(d) Step of cation exchanging treatment

The aqueous solution of acrylamide which has been subjected to the base treatment (c) is then treated with a cation exchange resin.

Various known cation exchange resins can be used in this step. They may be either strongly acidic cation exchange resins or weakly acidic cation exchange resins. These cation exchange resins may be gelled or porous. Free acid-type cation exchange resins are suitable. Specific examples of the cation exchange resins include Amberlite IR120B and IRC50 (tradenames for products of Rohm & Haas Company), Diaion SKIB PK208 and WK10 (tradenames for products of Mitsubishi Chemical Industries, Ltd.) and Lewatit SP100, SP112 and CNP80 (tradenames for products of Bayer AG).

The procedure of the cation exchanging treatment is described. The cation exchange resin is used in any of fixed, moving and suspended beds, but the fixed bed is the best. The concentration of the aqueous solution of acrylamide in the cation exchanging treatment is preferably in the range of 10 to 60% by weight for the same reason as in step (a). The temperature of the cation exchanging treatment is preferably not more than 40° C. in order to maintain the aqueous solution of acrylamide stable. Since the aqueous solution of acrylamide has its own acrylamide-precipitating temperature according to its concentration, the cation exchanging treatment temperature should be higher than the acrylamide-precipitating temperature. The speed of the treatment differs depending upon the type of the resin and the concentration and temperature of the aqueous solution of acrylamide, but, for example, in the case of the fixed bed method, the space velocity is preferably 1 to 20 $hr^{-1}$, more preferably 2 to 10 $hr^{-1}$.

The cation exchange resin which has lost its exchanging ability with the lapse of time is regenerated with chemicals in a customary manner, and reused. The point of time at which its exchanging ability has been lost can be determined from the quality of acrylamide finally obtained.

(e) Step of weakly basic anion exchanging treatment

The aqueous solution of acrylamide which has been subjected to the cation exchanging treatment in step (d) is then treated with a weakly basic anion exchange resin. Known methods for purifying acrylamide include a method for treating it with a strongly basic anion exchange resin. When this method is applied to this step of the present invention, the expected effect cannot be obtained.

Resins obtained by introducing a primary, secondary and/or tertiary amino group into a styrene/divinylbenzene copolymer are used as the weakly basic anion exchange resins. Specific examples include Amberlite IRA93 (a tradename for a product of Rohm & Haas Company), Lewatit MP62 and MP64 (tradenames for products of Bayer AG), and Diaion WA10 (a tradename for a product of Mitsubishi Chemical Industries, Ltd.). Preferably, these resins are used in the form of a free amine rather than in the form of a salt.

A specific procedure of performing the weakly basic anion exchanging treatment is described below. The weakly basic anion exchange resin can be used in any of a fixed bed, moving bed and suspended bed, but the fixed bed method is easiest to practice. The preferred concentration of the aqueous solution of acrylamide to be treated is in the range of 10 to 60% by weight for the same reason as in step (a) above. The treating temperature is preferably not more than 40° C. in order to maintain acrylamide stable. Since the aqueous solution of acrylamide has its own acrylamide-precipitating temperature according to its concentration, the treating temperature should be higher than the acrylamide-precipitating temperature. The speed of treatment varies depending upon the concentration, temperature, etc., of the aqueous solution of acrylamide. For example, in the case of the fixed bed method, the space velocity is preferably 0.5 to 10 $hr^{-1}$, more preferably 1 to 5 $hr^{-1}$.

The weakly basic anion exchange resin which has lost its exchanging ability with the lapse of time is regenerated with chemicals in a customary manner, and reused. The point of time at which its exchanging ability has been lost can be determined from the quality acrylamide finally obtained.

The process of the invention is characterized by the fact that the above five purifying steps are performed in the sequence mentioned above. If the above sequence is changed, no expected effect can be obtained, and such a changed sequence is outside the scope of the process of the invention. It is to be understood however that other purifying steps, such as treatment with activated carbon or concentration, may optionally be incorporated in the purifying process of this invention.

The advantages achieved by the practice of the process of the invention are:

(1) acrylamide is obtained which is suitable for the production of high-molecular-weight acrylamide polymers having a molecular weight of at least 10 million, particularly about 14 million, being easily soluble in water and having an unreacted monomer content of as low as about 0.2% by weight; and (2) stable acrylamide is obtained, which when stored for a long period of time, does not undergo degradation in quality but retains the aforesaid excellent quality.

If the sequence of the five purifying steps constituting the process of the invention is changed, these advantages cannot be obtained. For example, if the removal of acrylonitrile is performed after the cation exchanging treatment, the resulting acrylamide cannot give high-molecular-weight acrylamide polymers. If the weakly basic anion exchanging treatment is carred out after the copper eliminating treatment, the resulting acrylamide cannot give acrylamide polymers having good solubility in water. Furthermore, when the copper eliminating treatment is carried out after the base treatment, elimination of copper becomes difficult, and an attempt to polymerize the resulting acrylamide is not successful, leaving a large amount of the unreacted monomer.

The following Examples and Comparative Examples illustrate the present invention further.

EXAMPLE 1 AND COMPARATIVE EXAMPLES 1 TO 8

Catalyst for hydration reaction

A Raney copper alloy having a size smaller than 80 mesh was leached with sodium hydroxide in a customary manner, and washed to form a Raney copper catalyst. During the preparation and subsequent handling, the catalyst was kept from contact with an oxygen-containing gas such as air.

Catalytic hydration reaction

The above catalyst was charged into a stainless steel reactor having an agitator and a catalyst separator built therein, and acrylonitrile and water from which dissolved oxygen had been removed by using nitrogen gas were fed into the reactor and reacted. The reaction solution was agitated together with the catalyst and became a suspension. The suspension was then passed through the catalyst separator, and withdrawn from the reactor as a solution substantially free from the catalyst.

Treatment for removal of acrylonitrile

An acrylonitrile removing device was provided which consisted of a rectification tower packed with Rasching rings and an evaporator directly connected to its bottom. The solution obtained by the catalytic hydration reaction was fed to the top of the rectification tower and treated at a pressure of 100 mmHg. As a result, substantially all of the unreacted acrylonitrile and a part of the unreacted water were distilled off, and an aqueous solution of acrylamide having a concentration of about 50% by weight was recovered. This solution contained 10 ppm of acrylonitrile and 350 ppm of copper, both based on acrylamide (the same basis applies hereafter), and had a pH of about 6.5.

Copper eliminating treatment 150 ml of amberlite IR-120 B (a tradename for a strongly acidic cationic exchange resin made by Rohm & Hass Company), in a free acid form, was packed into a tubular glass column having an inside diameter of 20 mm. The solution obtained by the step of acrylonitrile removal was passed through the column at a rate of 800 ml/hr at room temperature. The resulting solution had a copper content of 0.01 ppm and a pH of 3.8. This copper eliminating treatment was continued for 24 hours.

Base treatment

A small amount of sodium hydroxide was continuously introduced into the aqueous solution of acrylamide flowing from the copper eliminating step to adjust the pH of the solution to about 12.8. The solution was introduced into the lower end of a column, 37 mm in inside diameter and 3 m in length, packed with stainless steel Raschig rings, and allowed to flow away from its upper end. This treatment was continued for 24 hours while adjusting the flow rate of the solution to about 800 ml/hr and the temperature of the column to about 20° C.

Cation exchanging treatment 200 ml of Lewatit SP112 (a tradename for a strongly acidic cation exchange resin made by Bayer AG), in a free acid form, was packed into a tubular glass column having an inside diameter of 20 mm, and the column was directly connected to the column used for the base treatment. The solution which had been subjected to the base treatment was introduced into this column at the same flow rate, and the cation exchanging treatment was continued for 24 hours at about 20° C.

Weakly basic anion exchanging treatment 200 ml of Lewatit MP-62 (a tradename for a weakly basic anion exchange resin made by Bayer AG), as a free base, was packed into a tubular glass column having an inside diameter of 20 mm. The column was directly coupled to the cation exchanging treatment column, and the aqueous solution of acrylamide which had been subjected to the cation exchanging treatment was introduced into this column at the same rate. This treatment was continued also for 24 hours at 20° C.

pH adjustment

Since the solution obtained by the weakly basic anion exchanging treatment was slightly basic or slightly acidic, sulfuric acid or sodium hydroxide was added to adjust the pH of the solution to about 7.0.

Test on storage of the aqueous solution of acrylamide

The solution obtained by the pH adjustment was immediately used in the following test. Or a part of it was put in a polyethylene bottle and stored at 40° C. for one month, and thereafter used in the following test.

Production of an acrylamide polymer

Using the aqueous solution of acrylamide obtained by the foregoing purifying procedure, an acrylamide polymer was produced by the following method. Water was added to the aqueous solution of acrylamide to adjust its concentration to 20% by weight. 500 g of the resulting solution of acrylamide was put in a 1-liter polyethylene container, and while maintaining it at 18° C., nitrogen gas was passed through it to remove dissolved oxygen in the solution. Immediately thereafter, the polyethylene container was put in a warmth-keeping block made of styrene foam. Then, $200 \times 10^{-6}$ mpm (the mole ratio of acrylamide) of 4,4'-azobis (sodium 4-cyanovalerate), $200 \times 10^{-6}$ mpm of diemthylaminopropionitrile and $80 \times 10^{-6}$ mpm of ammonium persulfate, each dissolved in a small amount of water, were quickly introduced into that sequence into the solution in the polyethylene container. Dissolved oxygen had previously been removed from these reagents by passing nitrogen gas, and before, during and also after the introduction of these reagents, a small amount of nitrogen gas was passed through the polyethylene container to prevent inclusion of oxygen gas. After an induction period of several minutes from the introduction of these reagents, a rise in the temperature of the inside of the polyethylene container was noted, and therefore, the feeding of nitrogen gas was stopped. After about 100 minutes when the temperature reached a maximum of about 70° C., the polyethylene container was taken out from the warmth-keeping block, dipped for 2 hours in water at 97° C., and then cooled by dipping in cold water. The resulting hydrogel of acrylamide polymer was divided into small lumps, minced by a mincing machine, dried with hot air at 100° C. for 2 hours, and pulverized for 3 minutes in a high-speed rotary blade-type pulverizer to give an acrylamide polymer as a dry powder. The powdery polymer was screened by a sieve to collect particles having a size of 32 to 42 mesh which were used as a polymer sample in the subsequent tests. (The water contents of the polymer samples in this and other Examples, determined as a decreased amount upon hot air drying at 125° C. overnight, were about 10%.) Methods for testing the acrylamide polymer:

The water solubility, molecular weight, standard viscosity and unreacted acrylamide content of the polymer sample were measured by the following methods.

Water solubility

Water (600 ml) was put in a 1-liter beaker, and while it was stirred by a stirring vane of a specified configuration, 0.66 g (pure content about 0.60 g) of the polymer sample was added. The mixture was stirred at 200 rpm for 2 hours. The resulting solution was filtered on a 150-mesh wire gauze, and the water-solubility of the polymer was determined by the amount of the insoluble portion and the filtrability of the solution and rated as follows:

o : completely or nearly completely dissolved.
Δ: there was an insoluble portion which, however, could be separated by filtration.
X: passing of the solution through the wire gauze was so slow that separation of the insoluble portion by filtration was virtually impossible.

Molecular weight

Aqueous solutions of the acrylamide polymer having different concentrations were prepared from the filtrate obtained by the procedure described in the section of "Water solubility". Sodium nitrate having a concentration corresponding to 1 M was added to the aqueous solutions, and the intrinsic viscosity was measured by using a capillary-type visco-meter. The molecular weight was calculated by using the following equation.

Intrinsic viscosity $= 3.73 \times 10^{-4}$ [weight average molecular weight]$^{0.66}$ Reports on Progress in Polymer Physics in Japan, 20, 5 (1977) suggests doubt in applying the above equation to acrylamide polymers having a molecular weight of at least 10 million. However, since this equation is in widespread use, the present inventors have also relied on it.

Stand viscosity

The filtrate obtained by the water-solubility test described above was a 0.1% by weight aqueous solution of the polymer when the water solubility of the polymer was good. Sodium chloride in a concentration corresponding to 1 M was added to the above aqueous solution, and its viscosity (standard viscosity) was measured by means of a BL-type visco-meter equipped with a BL adapter at 25° C. with the rotating speed of the rotor set at 60 rpm. Since the standard viscosity obtained by this method is customarily used as a value correlated with the molecular weight, it is also used in the Examples of the present application.

Content of the unreacted acrylamide

Methanol containing 20% by weight of water was added to the polymer sample, and the mixture was shaken overnight. The extract was subjected to gas chromatography to determine the content of the unreacted acrylamide.

Results of the tests on the acrylamide polymer:

Table 1 summarizes the results of the tests on the acrylamide polymer finally obtained by the aforesaid procedure.

Comparative Examples, the results of which are also shown in Table 1, were performed as follows:

Comparative Example 1

Example 1 was repeated except that in the treatment of removing acrylonitrile, the amount of the Raschig rings packed was reduced to half, and the acrylonitrile content of the aqueous solution of acrylamide was adjusted to 900 ppm.

Comparative Example 2

Example 1 was repeated except that the copper eliminating treatment was omitted.

Comparative Example 3

Example 1 was repeated except that the base treatment was omitted.

Comparative Example 4

Example 1 was repeated except that the cation exchanging treatment was omitted.

Comparative Example 5

Example 1 was repeated except that the weakly basic anion exchanging treatment was omitted.

Comparative Example 6

Example 1 was repeated except that the cation exchanging treatment and the weakly basic anion exchanging treatment were omitted.

Comparative Example 7

Example 1 was repeated except that the base treatment and the cation exchanging treatment were omitted.

Comparative Example 8

Example 1 was repeated except that the base treatment, the cation exchanging treatment and the weakly basic anion exchange treatment were omitted.

EXAMPLE 2 AND COMPARATIVE EXAMPLE 9

An aqueous solution of cupric sulfate was heated to 50° C., and an aqueous solution of sodium hypophosphite was added dropwise. After allowing the mixture to stand for a while, an aqueous solution of sodium hydroxide was added to prepare a copper catalyst. Using the resulting copper catalyst instead of the Raney copper in Example 1, the same tests as in Example 1 and Comparative Example 8 were performed respectively. The results are also shown in Table 1.

EXAMPLE 3 AND COMPARATIVE EXAMPLE 10

Copper oxide in the form of small pellets was filled in a stainless steel reaction tube and reduced with a gaseous mixture of hydrogen and nitrogen at about 200° C. to form reduced copper. Using this catalyst, the same catalytic hydration reaction as in Example 1 was carried out, and then the same tests as in Example 1 and Comparative Example 8 were performed respectively. The results are also shown in Table 1.

TABLE 1

| Run No. | Ex.1 | CEx.1 | CEx.2 | CEx.3 | CEx.4 | CEx.5 | CEx.6 | CEx.7 | CEx.8 | Ex.2 | CEx.9 | Ex.3 | CEx.10 |
|---|---|---|---|---|---|---|---|---|---|---|---|---|---|
| Copper catalyst used | Raney nickel | | | | | | | | | Decomposed copper | | Reduced copper | |
| Residual acrylonitrile (ppm) | 10 | 900 | 10 | 10 | 10 | 10 | 10 | 10 | 10 | 10 | 10 | 10 | 10 |
| Cu eliminating treatment | O | O | — | O | O | O | O | O | O | O | O | O | O |
| Base treatment | O | O | O | — | O | O | O | — | — | O | — | O | — |
| Cation exchanging treatment | O | O | O | O | — | O | — | O | — | O | — | O | — |
| Weakly basic anion exchanging treatment | O | O | O | O | O | — | — | O | — | O | — | O | — |
| Test results — Without storage — Water solubility | O | O | Δ | Δ | X | Δ | X | Δ | X | O | X | O | X |
| Standard viscosity (cps) | 6.0 | 5.0 | 5.8 | 5.9 | — | 6.0 | — | 5.9 | — | 6.0 | — | 5.9 | — |
| After storage at 40° C. for 1 month — Water solubility | O | O | X | X | X | Δ | X | X | X | O | X | O | X |
| Standard viscosity (cps) | 6.0 | 5.1 | — | — | — | 5.8 | — | — | — | 5.9 | — | 6.0 | — |

(*) Ex.: Example, CEx.: Comparative Example.

What we claim is:

1. A process for purifying a crude aqueous acrylamide solution obtained by catalytically hydrating acrylonitrile with water in the presence of a copper-based catalyst, the improvement which comprises subjecting the crude aqueous acrylamide solution, in sequence, to: (a) a step of distilling off substantially all of unreacted acrylonitrile, (b) a step of removing substantially all of copper contained therein, (c) a step of allowing the aqueous acrylamide solution to stand under basic conditions, (d) a step of subjecting the aqueous acrylamide solution to a cation exchange treatment and then (e) a step of subjecting the solution to a weakly basic anion exchange treatment.

2. The process of claim 1 wherein the concentration of acrylamide in the aqueous crude acrylamide solution is in the range of from 10 to 60% by weight.

3. The process of claim 1 wherein the amount of residual acrylonitrile in the aqueous solution of acrylamide is not more than 20 ppm.

4. The process of claim 1 wherein the amount of residual copper in the aqueous solution of acrylamide is not more than 25 ppm.

5. The process of claim 4 wherein the amount of residual copper in the aqueous solution of acrylamide is not more than 1 ppm.

6. The process of claim 1 wherein in step (c), a basic compound is added to the aqueous solution of acrylamide to adjust the pH of the solution to a range of 11.5 to 14.0, and the solution is allowed to stand at this pH.

7. The process of claim 6 wherein the solution is allowed to stand at a temperature of 40° to 10° C. for a period of 0.5 to 24 hours.

8. The process of claim 1 wherein the cation exchange resin treatment is carried out by using a strongly acidic cation exchange resin in H-form.

9. The process of claim 1 wherein the copper-based catalyst is Raney copper or reduced copper.

* * * * *